(12) United States Patent
Kowalik et al.

(10) Patent No.: US 6,447,791 B2
(45) Date of Patent: *Sep. 10, 2002

(54) USE OF ISOPARAFFIN EXTENDERS FOR CLEAR GEL COSMETIC COMPOSITIONS

(75) Inventors: Ralph M. Kowalik, Kingwood; Karen K. Kuo, Seabrook; Philip Merchant, Jr., Katy, all of TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/757,923

(22) Filed: Jan. 10, 2001

Related U.S. Application Data

(63) Continuation of application No. 09/395,904, filed on Sep. 14, 1999.
(60) Provisional application No. 60/116,705, filed on Jan. 22, 1999, and provisional application No. 60/100,608, filed on Sep. 16, 1998.

(51) Int. Cl.$^7$ .................................................. A61K 7/00
(52) U.S. Cl. ......................................... 424/401; 424/65
(58) Field of Search .................................. 424/401, 65

(56) References Cited

U.S. PATENT DOCUMENTS

| | | | |
|---|---|---|---|
| 4,322,400 A | 3/1982 | Yuhas | 424/59 |
| 4,673,570 A | 6/1987 | Soldati | 424/66 |
| 4,822,602 A | 4/1989 | Sabatelli | 424/65 |
| 4,900,542 A | 2/1990 | Parrotta, Jr. et al. | 424/66 |
| 5,162,378 A | 11/1992 | Guthauser | 514/785 |

FOREIGN PATENT DOCUMENTS

| | | | | |
|---|---|---|---|---|
| WO | WO 97/06777 | | 2/1907 | A61K/7/32 |
| WO | WO 92/05767 | | 4/1992 | A61K/7/34 |
| WO | WO94/18933 | | 9/1994 | A61K/7/00 |
| WO | WO 9706777 | * | 2/1997 | |
| WO | WO98/58623 | | 12/1998 | A61K/7/32 |

* cited by examiner

*Primary Examiner*—Konata George
(74) *Attorney, Agent, or Firm*—Andrew B. Griffis

(57) ABSTRACT

A clear cosmetic gel composition comprising: (a) an aqueous phase comprising: (i) water, and (ii) at least one cosmetically active ingredient; (b) a coupling agent; (c) an oil phase comprising: (i) a silicone-containing solvent, and (ii) an isoparaffin solvent having a boiling range between about 100 to 340° C., wherein the isoparaffin constitutes between about 1 to 75% by weight, of the total of the oil phase; and (d) silicone-containing surfactant.

34 Claims, No Drawings

USE OF ISOPARAFFIN EXTENDERS FOR CLEAR GEL COSMETIC COMPOSITIONS

CROSS REFERENCE TO RELATED APPLICATION

This Application is a continuation under Rule 1.53(b) of U.S. Ser. No. 09/395,904, filed Sep. 14, 1999, now allowed, which is based on U.S. Provisional Patent Application Ser. No. 60/100,608, filed Sep. 16, 1998, and U.S. Provisional Patent Application Ser. No. 60/116,705, filed Jan. 22, 1999.

The present invention generally relates to the use of isoparaffin solvents with silicone suffactants in the preparation of a clear gel antiperspirant or other cosmetic cream compositions. In particular, the present invention is directed to the replacement of 1 to 75%, preferably 25 to 50%, of the silicone solvent used in water-in-oil emulsion cosmetic compositions with an isoparaffin solvent. In particular, the present invention is directed to a liquid or semi-solid (for example, a gel or cream) cosmetic composition containing at least one active cosmetic material (e.g., deodorant active materials, antiperspirant active materials, sunscreen materials, insect repellents and anti-fungal agents), which leaves substantially no visible residue on the skin and which has good cosmetic properties.

BACKGROUND OF THE INVENTION

Antiperspirant and deodorant products are well-known in the cosmetic art. They are generally used by rubbing an area of the body such as the underarm to apply a layer of the composition to the skin which reduces odor and/or perspiration. It is desirable that such products have aesthetic characteristics of non-crumbling, smoothness, non-oiliness and non-tackiness. Clarity of such products is a long-sought desirable aesthetic characteristic. Another desirable characteristic is that no readily visible residue as, e.g., a white layer, be left on the skin after the deodorant or antiperspirant is applied.

Antiperspirant and deodorant products have appeared in the marketplace in various dosage forms, such as sticks, gels, roll-ons, aerosols and creams. Generally, these dosage forms include a solution of the active ingredient in a suitable solvent, a suspension of the active ingredient in a non-solvent, or a multiphase dispersion or emulsion in which a solution of the active ingredient is dispersed in some continuous phase or in which the solubilized active ingredient constitutes the continuous phase.

The stick form has become the dominant antiperspirant dosage form in the United States market, constituting more than 50% of total antiperspirant sales, and is popular to varying degrees globally. Cosmetically acceptable antiperspirant sticks typically consist of a suspension of spray-dried active antiperspirant material in vehicles such as cyclomethicone, with a waxy substance such as stearyl alcohol, alone or in combination with castor wax, gelling or thickening the suspension sufficiently to create a suitable stick.

The stick form can be distinguished from a gel or a paste in that in a stick, the formulated product can maintain its shape for extended time periods outside the package, the product not losing its shape significantly (allowing for some shrinkage due to solvent evaporation).

The hard stick dosage form, although widely accepted by the consumer, suffers from leaving a white residue on skin after application, and can cause staining of fabric, which is considered to be undesirable, particularly by female consumers. The gel dosage form can be formulated to reduce and/or eliminate the white residue.

One such clear gel antiperspirant is set forth in International Patent Application No. WO 92/05767, published on Apr. 16, 1992 (The Gillette Company), which is incorporated herein by reference. This patent application pertains generally to a clear gel-type cosmetic product which includes an emulsion with an oil phase and a water phase that includes an incorporated active ingredient. The oil phase preferably makes up about 10 to 25% of the product and includes an emulsifier which when properly mixed with the water phase components yields a water-in-oil emulsion. The oil phase is typically a blend of liquids and includes a polyorganosiloxane (e.g., dimethicone) and a silicone emulsifying agent. A particularly suitable emulsifying agent is a polyether substituted silicone of cyclomethicone and dimethicone copolyol. This emulsifier is useful for preparing stable water-in-oil silicone emulsions where silicone makes up a large portion of the oil phase, and is a dispersion of a silicone surfactant (i.e., dimethicone copolyol), i.e., 10% silicone surfactant in cyclomethicone (i.e., a silicone solvent). The water phase includes one or more polar species such as water, propylene glycol, sorbitol and ethanol. The water phase includes, in solution, a deodorant and/or antiperspirant active ingredient such a triclosan, benzethonium chloride and/or an astringent salt of aluminum or zirconium, such as aluminum chlorohydrate or aluminum zirconium tetrachlorohydrex-glycine. The gel can also contain additional cosmetic ingredients such as emollients, colorants, fragrances, and preservatives.

Some examples of conventional gel antiperspirants and deodorants are set forth below:

| Antiperspirant | |
|---|---|
| Water Phase | |
| Water | 37.01% |
| Aluminum Chlorohydrate | 30.00% |
| Ethanol | 10.00% |
| Propylene Glycol | 4.99% |
| Oil Phase | |
| Dimethicone | 9.85% |
| Cyclomethicone & Dimethicone Copolyol | 8.00% |
| Fragrance | |
| Fragrance | 0.15% |
| Deodorant | |
| Water Phase | |
| Water | 33.25% |
| Sorbitol | 14.00% |
| Ethanol | 12.00% |
| Propylene Glycol | 22.50% |
| Triclosan | 0.25% |
| Sodium Hydroxide | 0.02% |
| Oil Phase | |
| Dimethicone | 9.70% |
| Cyclomethicone & Dimethicone Copolyol | 8.00% |
| Fragrance | |
| Fragrance | 0.30% |

International Patent Application No. WO 97/06777, which is incorporated herein by reference, also discloses a clear cosmetic gel composition which includes: (1) an aqueous phase containing water and at least one cosmetically active ingredient, (2) an oil phase containing a high refractive index material, (3) at least one coupling agent to bring the aqueous phase and the oil phase into a homogeneous composition, and (4) an alkoxylated, alkyl substituted siloxane surface active agent in an amount sufficient to form the composition into a water-in-oil emulsion. The oil phase includes a volatile silicone fluid, a non-volatile silicone fluid and an emollient. The emollient is preferably phenyl trimethicone.

U.S. Pat. No. 4,900,542 (Parrotta, Jr., et al.), which issued on Feb. 13, 1990 and which is incorporated herein by reference, discloses a process for preparing uniform, clear, microcrystalline emulsion antiperspirant compositions of gel-like consistency comprising: mixing the antiperspirant active material with water, charging the aqueous phase into an oil-alcohol phase containing a volatile silicone, a silicone emulsifier, a non-volatile emollient and a coupling agent, heating the resultant mixture with agitation until a uniform mixture is obtained, homogenizing the mixture and passing the homogenized mixture to a holding tank or directly to a filter.

The clear gel antiperspirants and deodorants described above are based on water-in-oil emulsions which are stabilized with a silicone surfactant. The silicone surfactant is commercially available as a 10 wt. % solution in a volatile silicone solvent, such as cyclomethicone (also known as decamethycyclopentasiloxane and/or octamethylcyclotetrasiloxane). The present inventors have unexpectedly discovered that by diluting a concentrated version of the silicone surfactant with an isoparaffin solvent, clear gel antiperspirants or deodorants can be formed having the same appearance (i.e., clarity and viscosity) at substantially lower cost and at higher indices of refraction.

Furthermore, the present inventors have discovered that viscous, non-volatile silicone fluids, e.g., dimethicone, can be partially replaced with isoparaffins and maintain the viscosity of the gel's oil phase, while also reducing the cost of the overall composition.

The present invention also provides many additional advantages which shall become apparent as described below.

SUMMARY OF THE INVENTION

A clear cosmetic gel composition comprising: (a) an aqueous phase comprising: (i) water, and (ii) at least one cosmetically active ingredient; (b) a coupling agent; (c) an oil phase comprising: (i) a silicone-containing solvent, and (ii) an isoparaffin solvent having a boiling range between about 100 to 340° C., wherein the isoparaffin constitutes between about 1 to 75% by weight, of the total of the oil phase; and (d) silicone-containing surfactant.

The silicone-containing surfactant is preferably an alkoxylated, alkyl substituted siloxane surface active agent, e.g., dimethicone copolyol or a mixture of dimethicone copolyol and cyclomethicone. This silicone-containing surfactant is present in an amount between about 0.2 to 2% by weight, of the total weight of the composition. The coupling agent is present in an amount between about 10 to 30% by weight, of the total weight of the composition.

The aqueous phase comprises water in an amount between about 20 to 70% by weight, of the total weight of the composition. The oil phase comprises a silicone-containing solvent which includes a volatile silicone fluid and a non-volatile silicone fluid. The volatile silicone fluid is preferably a cyclomethicone and the non-volatile silicone fluid is preferably dimethicone. The preferred mixture of the oil phase and the silicone-containing surfactant comprises between about 10 to 30% by weight, of the total weight of the composition, and the mixture of the aqueous phase and the coupling agent comprises between about 70 to 90% by weight, of the total weight of the composition.

Optionally, the isoparaffin can replace at least a portion of the dimethicone such that the oil phase has essentially the same viscosity as the original oil phase. The molecular weight of the dimethicone may need to be simultaneously increased to achieve this viscosity.

By isoparaffin is meant a saturated aliphatic hydrocarbon whose molecules have at least one carbon atom bonded to at least three other carbon atoms or at least one side chain (i.e., a molecule having one or more tertiary or quaternary carbon atoms), and preferably wherein the total number of carbon atoms per molecule is in the range between about 8 to 20, more preferably 10 to 20. Various isomers of each carbon number will typically be present in the solvent. The isoparaffins may also include cycloparaffins with branched side chains, generally as a minor component of the isoparaffin solvent. The isoparaffin solvent may contain molecules have a carbon number (e.g., a narrow cut such as isomers having a range between about $C_{10}$ to $C_{12}$, or a wide cut such as isomers having between about $C_{11}$ to $C_{18}$). The vapor pressure of the isoparaffin is also preferably not greater than 2 mm Hg at 20° C. for antiperspirant and deodorant products. Preferably, the isoparaffin constitutes between about 25 to 50% by weight, of the total of the oil phase.

The clear cosmetic gel composition of the present invention may further comprise at least one additional additive selected from the group consisting of: emollients, humectants, antiseptics, antioxidants, chelating agents, ultraviolet absorbers, colorants, fragrances and preservatives. This composition is preferably either a deodorant, antiperspirant, sunscreen, insect repellent or anti-fungal agent.

The present invention also pertains to a process for preparing a clear cosmetic gel composition comprising mixing the following: an aqueous phase comprising: (i) water, and (ii) at least one cosmetically active ingredient; a coupling agent; an oil phase comprising: (i) a silicone-containing solvent, and (ii) an isoparaffin solvent having a boiling range between about 100 to 340° C., wherein the isoparaffin constitutes between about 1 to 75% by weight, of the total of the oil phase; and silicone-containing surfactant.

Another embodiment of the present invention includes a clear cosmetic gel composition comprising: (a) an aqueous phase comprising: (i) water, and (ii) at least one cosmetically active ingredient; (b) a coupling agent; (c) an oil phase comprising: a silicone-containing solvent comprising a volatile silicone fluid and a non-volatile silicone fluid, and wherein at least a portion of the non-volatile silicone fluid is replaced with an isoparaffin solvent having a boiling range between about 200 to 340° C., wherein the viscosity of the non-volatile silicone/isoparaffin solution is in the range between about 10 to 100 cps at a temperature between about 20 to 25° C.; and (d) silicone-containing surfactant. Preferably, the volatile silicone fluid is cyclomethicone and the non-volatile silicone fluid is dimethicone. Optionally, the isoparaffin has a flash point in the range between about 60 to 150° C. and the non-volatile silicone fluid has a viscosity of no greater than 10,000 cSt.

Other and further objects, advantages and features of the present invention will be understood by reference to the following specification in conjunction with the annexed drawings, wherein like parts have been given like numbers.

DESCRIPTION OF THE PREFERRED EMBODIMENTS

The following $C_8$ to $C_{20}$ isoparaffins are useful as solvent extenders in the present application. Table 1 below sets forth a series of commercially available isoparaffin solvents and their associated physical properties which can be used in this case.

TABLE 1

| Isoparaffin | Distillation Range (° C.) | Flash Point TCC (° C.) | Specific Gravity* | Composition, Wt. % | |
|---|---|---|---|---|---|
| | | | | Saturates | Aromatic |
| Isopar ® E | 117–136 | 7 | 0.72 | 100 | <0.01 |
| Isopar ® G | 161–176 | 41 | 0.75 | 100 | <0.01 |
| Isopar ® H | 178–188 | 54 | 0.76 | 100 | <0.01 |
| Isopar ® K | 179–196 | 55 | 0.76 | 100 | <0.01 |
| Isopar ® L | 188–207 | 62 | 0.77 | 100 | <0.01 |
| Isopar ® M | 223–254 | 92 | 0.79 | 99.9 | 0.01 |
| Isopar ® V | 272–311 | 130 | 0.82 | 99.9 | <0.1 |

*Specific gravity as measured @ 15.6/15.6° C.

Throughout the present disclosure, the present invention is described primarily in connection with a clear soft gel antiperspirant composition. However, the present invention is not limited to soft gel compositions or to antiperspirant compositions. For example, compositions according to the present invention can be clear deodorant compositions. Moreover, depending on additional or other active ingredients included in the composition, the composition can also be an emollient composition, an analgesic (methyl salicylate) composition, a sunscreen composition, etc. Various active materials incorporated in cosmetic compositions are disclosed in U.S. Pat. No. 4,322,400 to Yuhas, the contents of which are incorporated herein by reference in their entirety.

Throughout the present specification, "active antiperspirant" and "active deodorant" materials are discussed. Both types of materials contribute to reduction of body malodor. By reduction of body malodor, we mean that, generally, there is less body malodor after application of a composition to the person's skin as compared to the person's body malodor without application of the composition. Such reduction can be due to a masking of the malodor, absorption and/or chemical reaction of the malodorous material, reduction of levels of the bacteria producing the malodorous material, e.g., from perspiration, reduction of perspiration, etc. The antiperspirant active materials, when utilized in an antiperspirant effective amount in the composition, act to reduce body malodor by reducing production of perspiration; however, these antiperspirant active materials can also have a deodorant function, e.g., as an antimicrobial agent. The deodorant active materials do not substantially reduce the production of perspiration, but reduce malodor in other ways, e.g., as fragrances masking the malodor or reducing the malodor intensity, as odor absorbents, as antimicrobial agents, as agents chemically reacted with malodorous materials, etc.

A desired feature of the present invention is that a clear, or transparent, cosmetic gel composition (e.g., clear or transparent deodorant or antiperspirant gel composition) can be provided. The term clear or transparent (that is clarity), according to the present invention, is intended to connote its usual dictionary definition; thus, a clear, e.g., cosmetic gel composition at the present invention allows ready viewing of objects behind it. By contrast, a translucent composition allows light to pass through, but causes the light to be so scattered that it will be impossible to see clearly objects behind the translucent composition.

The present invention contemplates a clear cosmetic gel composition which is a water-in-oil emulsion. The aqueous phase of this emulsion contains water and at least one cosmetically active ingredient, with the cosmetically active ingredient being in the composition in an amount so as to have a cosmetic effect. The oil phase of the emulsion includes a high refractive index material (a material having a refractive index in the range of 1.40–1.50) and desirably also includes silicone surfactants, and preferably contains both volatile and non-volatile silicone solvents. Optionally, the compositions according to the present invention also include at least one coupling agent to bring the aqueous phase and the oil phase into a homogeneous composition. Moreover, the clear cosmetic gel composition of the present invention, which is in the form of a macro-emulsion as contrasted to a micro-emulsion, does not need to contain wax or gelling agents such as soaps, cellulosic materials or algenites.

The gel emulsions according to the present invention are stable and optically clear, are cosmetically elegant, and are capable of being delivered from a suitable applicator package. They are easily applied to the skin and have a smooth, silky feel and a cool sensation, yet are fast-drying and non-tacky. These compositions of the present invention may be prepared by a batch process, or a continuous or semi-continuous process, and the processes yield compositions which are stable, highly efficacious and possess excellent aesthetic qualities.

Where the composition is an antiperspirant gel composition, any of the known antiperspirant active materials can be utilized in the composition at the present invention. Suitable materials which may be mentioned by way of example include aluminum chlorohydrate, aluminum chloride, aluminum sesquichlorohydrate, aluminum-zirconium hydroxychlorides, complexes or adducts of the above-mentioned active ingredients with glycol, such as propylene glycol, and combinations thereof. Known aluminum-zirconium salts in combination with neutral amino acids, such as glycine (e.g., aluminum-zirconium tetrachlorohydroxy) can also be used. Generally, any of the Category I active antiperspirant ingredients, listed in the Food and Drug Administration's Monograph on Antiperspirant Drug Products for overall-the-counter human use (Oct. 10, 1973) can be used. In addition, any new ingredient, not listed in the Monograph, such as aluminum nitrohydrate and its combination with zirconyl hydroxychlorides and nitrates, or aluminum-stannous chlorohydrates, can be incorporated as an antiperspirant active ingredient in antiperspirant compositions according to the present invention.

The preferred antiperspirant materials include aluminum zirconium tetrachlorohydrate and aluminum chlorohydrate.

The amount of active component that can be used will vary with the particular active ingredient incorporated. As a general rule, an antiperspirant product should contain an active antiperspirant material in an amount anywhere from about 10% to about 35% by weight, of the total weight of the composition, more preferably from about 20% to about 30% by weight, of the total weight of the composition. The active antiperspirant material utilized in the compositions of the present invention can be pre-dissolved in water or in another solvent (for example, in propylene glycol) or can be in powdered form, and may be buffered or unbuffered. Preferably, the antiperspirant materials are present in solution in a solvent therefor.

Where a deodorant active material is utilized, any deodorant active material which can be dissolved in the aqueous phase can be utilized. Illustratively, the deodorant active material can be 2,4,4'-trichloro-2'-hydroxy diphenyl ether (triclosan), and/or benzethonium chloride. Where the deodorant ingredient is used in place of the antiperspirant active ingredient, a deodorant gel composition (rather than an antiperspirant gel composition) would be provided.

Amounts of cosmetically active ingredients incorporated are those sufficient to have a cosmetic effect. For example, where a deodorant active ingredient such as triclosan is incorporated, amounts thereof as conventionally used in the art can be incorporated in the composition according to the present invention.

The aqueous phase includes one or a combination of various polar species, and includes at least water (refractive index of 1.3333). Other polar species include polyhydric alcohols and derivatives thereof (e.g., esters and ethers thereof). Illustratively, water can be included in the composition in an amount in the range of 20% to 70% by weight, of the total weight of the composition.

At least one coupling agent is included in the composition of the present invention. Such coupling agent is illustratively (but not limited to) the following:

| Coupling Agents | |
| --- | --- |
| Ethyl alcohol | Ethylene glycol monoethyl ether |
| 2-ethylhexanol | Diethylene glycol monoethyl ether |
| Ethylene carbonate | Propoxylated oleyl alcohol |
| N-methylglucamine | Butyl stearate |
| Linear ethoxylated polymer of methanol | Butyl myristate |
| | Isopropyl alcohol |
| SD-40 alcohol | PPG-(2-5) lanolate |
| PPG (2-8) myristyl ether | PPG-(2-8) isostearate |
| PPG (2-8) lauryl ether | Propylene glycol (2) methyl ether |
| Dipropylene glycol | PPG-(2-3) methyl ether |
| PPG (2-10) cetyl ether | PPG-14 butyl ether |
| PEG-6 diisopropyl adipate | Ethoxylated (2-20 moles) glucose |
| Methoxy PEG-22 dodecyl-glycol copolymer | Propoxylated (2-20 moles) glucose |
| | PPG-15 Stearyl ether |
| PEG-30 Glyceryl monoacetate | PPG-(5-20) methyl glucose ether |
| Sorbitol | Isoprene glycol |
| PEG-3 oleyl ether phosphate | Propylene carbonate |
| PEG-(2-5) oleyl ether | Glycerine |

This coupling agent acts to stabilize the emulsion and also acts as a clarifying agent. Moreover, various of these coupling agents, such as SD-40 alcohol, aid in drying and has a cooling effect, providing advantageous aesthetic properties for the composition.

The coupling agent is preferably a low molecular weight alcohol such as, but not limited to, an alcohol having from about 2 to about 10 carbon atoms, preferably from about 2 to about 4 carbon atoms; or a glycol such as, but not limited to, propylene glycol, ethylene glycol, isoprene glycol and dipropylene glycol; glycerine, sorbitol and/or propylene carbonate. The coupling agent can be one compound or a mixture of compounds.

Illustratively, the coupling agent is present in an amount of from about 10% to about 30% by weight, preferably from about 14% to about 25% by weight, of the total weight of the composition.

The oil phase according to the present invention is desirably, a silicone oil/isoparaffin solution, so as to provide a water-in-oil emulsion. The total of oil phase and siloxane surface active agent preferably makes up from about 8% to about 30% by weight, of the total weight of the composition. This surface active agent is an emulsifier which, when properly mixed with the aqueous phase components, oil phase components and coupling agents, yields a water-in-oil emulsion. The oil phase is desirably a blend of liquids.

The oil phase can include, illustratively, a volatile silicone solvent such as cyclomethicone and a non-volatile silicone fluid such as dimethicone; however, the composition of the present invention need not include both the volatile and non-volatile silicone fluids. Where the composition includes the volatile silicone it is preferred that such volatile silicone be a polydimethylcyclosiloxane, present in an amount up to about 18% by weight, of the total weight of the composition, preferably from about 4% to about 12% by weight, of the total weight of the composition. Preferred polydimethylcyclosiloxanes are those named cyclomethicones. Preferred cyclosiloxanes are octamethylcyclotetrasiloxane, decamethylcyclopentasiloxane and blends of tetramer and pentamer cyclomethicones. Commercial cyclosiloxanes which can be utilized as part of the composition of the present invention include, illustratively Dow Corning 244 Fluid, Dow Corning 245 Fluid, Dow Corning 344 Fluid and Dow Corning 345 Fluid (from Dow Corning Corp.), and SF1202, SF1204 and SF1173 (from General Electric Company).

The oil phase preferably is a mixture of a volatile silicone fluid (such as cyclomethicone), a non-volatile silicone fluid (such as dimethicone), and an isoparaffin. The relatively higher indices of refraction (i.e., 1.402–1.450) of the isoparaffin of the present invention relative to cyclomethicone and dimethicone may permit a reduction or elimination of very expensive high index of refraction silicone oils such as phenyl trimethicone.

The alkoxylated, alkyl substituted siloxane surface active agent is preferably, but not limited to, a dimethicone copolyol. An illustrative alkoxylated silicone-containing surfactant utilizable according to the present invention is cetyl dimethicone copolyol referred to in U.S. Pat. No. 5,162,378 to Guthauser. Illustratively, the alkoxylated, alkyl substituted siloxane surface active agent is included in the composition in an amount of 0.2% to 2% by weight, of the total weight of the composition.

A specific cyclomethicone-dimethicone copolyol fluid which can be utilized to provide the alkoxylated silicone containing surface active agent is a mixture of cyclomethicone and dimethicone copolyol designated as DC3225C from Dow Corning Corp or SF1328 from General Electric Company. This is a polyether substituted silicone of cyclomethicone and dimethicone copolyol (refractive index (RI)= 1.3994). This DC3225C, which is an emulsifying agent, is useful for preparing stable water-in-oil emulsions where a silicone makes up a large portion of the oil phase, and is a dispersion of a silicone sufactant (dimethicone copolyol) (10% by wt.) in cyclomethicone (Dow Corning 344 Fluid) (90% by wt.).

The mixture of cyclomethicone and dimethicone copolyol fluid is present in the composition, illustratively, in an amount of from about 4% to about 20% by weight, of the total weight of the composition. The unique aspect according to the present invention is that between 25–50% of the cyclomethicone in the dimethicone copolyol dispersion is replaced with at least one isoparaffin without any concomitant loss of properties, but with the added cost benefits associated with the use of much cheaper isoparaffins.

Various materials which can be incorporated in the water-based phase and in the oil-based phase are listed in International Patent Application Publication No. WO 97/06777, which is incorporated herein by reference, for example, emollients, humectants, antiseptics, preservatives, antioxidants, chelating agents, and U.V. absorbers.

While not limiting, in preferred embodiments the mixture of oil phase and alkoxylated, alkyl substituted siloxane surface active agent comprises from about 10% to about 30% by weight, of the total weight of the composition, and the combination of aqueous phase and coupling agents make up from about 70% to about 90% by weight, of the total weight of the composition.

EXAMPLE 1

Samples 1 and 2 are comparative samples of the prior art and Samples 3–6 are samples according to the present invention.

| Sample | 1 | 2 | 3 | 4 | 5 | 6 |
|---|---|---|---|---|---|---|
| Water Phase (wt. %) | | | | | | |
| Rezal 36 (45% solids) | 48.22 | 45.07 | 42.86 | 48.18 | 43.17 | |
| Renzal 36GP (100% Solids) | | | | | | 21.48 |
| DI Water | 12.10 | 11.17 | 10.63 | 11.94 | 10.84 | 35.46 |
| Propylene Glycol | 6.03 | 7.89 | 5.36 | 8.03 | 15.18 | 15.49 |
| Tripropylene Glycol | 7.53 | 11.46 | 17.95 | 7.53 | 6.82 | 7.10 |
| SD Alcohol | 8.04 | 7.51 | 7.14 | 6.02 | 5.47 | 2.46 |
| Oil Phase (wt. %) | | | | | | |
| Dimethicone Copolyol* | 9.04 | — | — | — | — | 9.00 |
| Dimethicone Copolyol** | — | 8.45 | — | — | — | — |
| Dimethicone Copolyol*** | — | — | 2.01 | 2.26 | 2.25 | — |
| Cyclo-methicone | — | — | 2.441 | 4.75 | 2.7 | — |
| Isopar® L | — | — | 3.62 | 2.26 | 4.05 | — |
| Isopar® M | — | — | — | — | — | 2.90 |
| Dimethicone (DC 200:50 cSt) | 7.28 | 6.81 | 6.47 | 7.28 | 7.24 | — |
| Dimethicone (GE 96-200) | | | | | | 4.35 |
| Phenyl trimethicone | 1.76 | 1.64 | 1.56 | 1.76 | 1.75 | 1.75 |
| Total (wt. %) | 100 | 100 | 100 | 100 | 100 | 100 |
| % of Silicone Fluid Replaced by Isoparaffin | 0 | 0 | 50 | 25 | 50 | 40 |
| n (oil phase) | 1.4055 | 1.4049 | 1.4138 | 1.4103 | 1.4135 | 1.4106 |
| n (water phase) | 1.4061 | 1.4048 | 1.4143 | 1.4103 | 1.4133 | 1.4107 |
| $\Delta$ n (oil-$H_2O$) | −0.0005 | 0.0001 | −0.0005 | 0 | 0.0002 | −0.0001 |
| Relative clarity (0 best) | 2 | 1 | 3 | 0 | 1 | 1 |
| Relative viscosity | Med. | Med. | High | Low | High | High |
| Oil/Water by wt. | 0.221 | 0.203 | 0.191 | 0.224 | 0.219 | 0.220 |

*Dimethicone Copolyol (DC 3225C)
**Dimethicone Copolyol (GE SF 1328)
***Dimethicone Copolyol (GE 407-2517)

Table 1 above includes example 6 with Isopar® M plus a higher molecular weight/viscosity dimethicone (GE 96-200, 200 cSt) substituted for a lower molecular weight/viscosity dimethicone (DC 200: 50 cSt) such as that used in control sample 1. In all examples 1 through 6, the ingredients of the oil and water phases are first mixed separately, and then emulsified using a high-speed paint mixer. Indices of refraction of the oil and water phases have been matched to form relatively clear gels. The results show improved visual clarity as the difference between oil and water phase indices of refraction ($\Delta$n) becomes smaller.

The first embodiment according to the present invention set forth above is directed to the economic advantages associated with partially replacing or extending volatile silicone fluids such as cyclomethicone with isoparaffin solvents in clear gel antiperspirants. The second embodiment more clearly set forth below relates to the use of isoparaffins as lower cost extenders for less volatile silicone fluids that are used in personal care products generally. These silicone fluids are typically polydimethylsiloxanes (i.e., dimethicones) of various molecular weights and viscosities. The present inventors have discovered that by replacing part of the dimethicone with an isoparaffin solvent and, if necessary, by increasing the molecular weight of the dimethicone, the extended dimethicone solution can have properties similar to the original dimethicone fluid by itself.

The present invention pertains to a multitude of other combinations of isoparaffins and dimethicones in which the choice of component concentrations and viscosities provide properties that match specific application needs. One important consideration of the present invention is to minimize the skin irritation potential of the isoparaffins. In this regard, higher boiling isoparaffin materials such as Isopar® V (sold by Exxon Chemical Company) are preferred based on their extremely low skin irritation potential. When more volatile isoparaffins are used, their concentrations should be appropriately limited to avoid potential skin irritation.

Another important aspect in the selection of isoparaffin/dimethicone blends is the miscibility of the two fluids. Isoparaffins having boiling ranges between about 115 and 310° C. (i.e., Isopar® E to Isopar® V, both sold by Exxon Chemical Company) have been found to be fully miscible with dimethicones having viscosities up to 10,000 cSt. Combinations of higher molecular weight dimethicones and/or higher boiling isoparaffins may not be miscible.

EXAMPLE 2

Replacing volatile silicone fluids with isoparaffins is shown herebelow, wherein a portion of a low viscosity (10 cSt) dimethicone (e.g., Dow Corning's DC-225 Fluid) with Isopar® V (14.8 cSt). This would be a direct substitution of an isoparaffin for part of a dimethicone.

EXAMPLE 3

Another example of the present invention would be to replace a 350 cSt viscosity dimethicone (e.g., SF96-350, sold by General Electric) with a solution containing 55 wt. % Isopar® M (sold by the Exxon Chemical Company) and 45 wt. % Viscasil® 10,000 having a viscosity of 10,000 cSt (sold by General Electric Company). This solution has about the same viscosity as the original SF96-350 fluid as measured with a bubble tube viscometer.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications which come within the scope of the appended claims.

What is claimed is:

1. A clear cosmetic gel composition comprising:
   (a) an aqueous phase comprising: (i) water, and (ii) at least one cosmetically active ingredient;
   (b) a coupling agent;
   (c) an oil phase comprising: (i) a silicone-containing solvent, and (ii) an isoparaffin solvent having a boiling range between about 100 to 340° C., wherein said isoparaffin constitutes between about 1 to 75% by weight, of the total of said oil phase; and (d) silicone-containing surfactant.

2. The composition according to claim 1 wherein said silicone-containing surfactant is an alkoxylated, alkyl substituted siloxane surface active agent.

3. The composition according to claim 2 wherein said silicone-containing surfactant is dimethicone copolyol or a mixture of dimethicone copolyol and cyclomethicone.

4. The composition according to claim 1 wherein said silicone-containing surfactant is present in an amount between about 0.2 to 2% by weight, of the total weight of said composition.

5. The composition according to claim 1 wherein said coupling agent is present in an amount between about 10 to 30% by weight, of the total weight of said composition.

6. The composition according to claim 1 wherein said silicone-containing solvent comprises a volatile silicone fluid and a non-volatile silicone fluid.

7. The composition according to claim 6 wherein said volatile silicone fluid is cyclomethicone.

8. The composition according to claim 6 wherein said non-volatile silicone fluid is dimethicone.

9. The composition according to claim 1 wherein the mixture of said oil phase and said silicone-containing surfactant comprises between about 10 to 30% by weight, of the total weight of said composition, and the mixture of said aqueous phase and said coupling agent comprises between about 70 to 90% by weight, of the total weight of said composition.

10. The composition according to claim 8 wherein said isoparaffin replaces at least a portion of said dimethicone such that said dimethicone and isoparaffin solvents have a viscosity in the range between about 10 to 100 cps at a temperature between about 20 to 25° C.

11. The composition according to claim 1 wherein said isoparaffin solvent is a saturated aliphatic hydrocarbon containing at least one side chain, and wherein the total carbon atoms are in the range between about 8 to 20.

12. The composition according to claim 1 wherein said isoparaffin constitutes between about 25 to 50% by weight, of the total of said oil phase.

13. The composition according to claim 1 wherein the vapor pressure of said isoparaffin solvent is not greater than 2 mm Hg at 20° C.

14. The composition according to claim 1 further comprising at least one additional additive selected from the group consisting of: emollients, humectants, antiseptics, antioxidants, chelating agents, ultraviolet absorbers, colorants, fragrances and preservatives.

15. The composition according to claim 1 wherein said isoparaffin solvent has a flash point between about −10 to 150° C.

16. The composition according to claim 1 wherein said composition is a deodorant, antiperspirant, sunscreen, insect repellent or anti-fungal agent.

17. A process for preparing a clear cosmetic gel composition comprising mixing the following:

an aqueous phase comprising: (i) water, and (ii) at least one cosmetically active ingredient;

a coupling agent;

an oil phase comprising: (i) a silicone-containing solvent, and (ii) an isoparaffin solvent having a boiling range between about 100 to 340° C., wherein said isoparaffin constitutes between about 1 to 75% by weight, of the total of said oil phase; and silicone-containing surfactant.

18. The process according to claim 17 wherein said silicone-containing solvent comprises a volatile silicone fluid and a non-volatile silicone fluid.

19. The process according to claim 18 wherein said volatile silicone fluid is cyclomethicone.

20. The process according to claim 18 wherein said non-volatile silicone fluid is dimethicone.

21. The process according to claim 17 wherein said isoparaffin solvent is a saturated aliphatic hydrocarbon containing at least one side chain, and wherein the total carbon atoms are in the range between about 8 to 20.

22. The process according to claim 17 wherein said isoparaffin constitutes between about 25 to 50% by weight, of the total of said oil phase.

23. The process according to claim 17 wherein the vapor pressure of said isoparaffin solvent is not greater than 2 mm Hg at 20° C.

24. The process according to claim 17 further comprising mixing at least one additional additive selected from the group consisting of: emollients, humectants, antiseptics, antioxidants, chelating agents, ultraviolet absorbers, colorants, fragrances and preservatives.

25. The process according to claim 17 wherein said composition is a deodorant, antiperspirant, sunscreen, insect repellent or anti-fungal agent.

26. A clear cosmetic gel composition comprising:

(a) an aqueous phase comprising: (i) water, and (ii) at least one cosmetically active ingredient;

(b) a coupling agent;

(c) an oil phase comprising: a silicone-containing solvent comprising a volatile silicone fluid and a non-volatile silicone fluid, and wherein at least a portion of said non-volatile silicone fluid is replaced with an isoparaffin solvent having a boiling range between about 200 to 340° C., wherein the viscosity of said isoparaffin and non-volatile silicone fluid is in the range between about 10 to 100 cps at a temperature between about 20 to 25° C.; and (d) silicone-containing surfactant.

27. The composition according to claim 26 wherein said volatile silicone fluid is cyclomethicone.

28. The composition according to claim 26 wherein said non-volatile silicone fluid is dimethicone.

29. The composition according to claim 26 wherein said isoparaffin solvent is a saturated aliphatic hydrocarbon containing at least one side chain, and wherein the total carbon atoms are in the range between about 8 to 20.

30. The composition according to claim 26 wherein said isoparaffin constitutes between about 25 to 50% by weight, of the total of said oil phase.

31. The composition according to claim 28 wherein the vapor pressure of said isoparaffin solvent is not greater than 2 mm Hg at 20° C.

32. The composition according to claim 26 further comprising mixing at least one additional additive selected from the group consisting of: emollients, humectants, antiseptics, antioxidants, chelating agents, ultraviolet absorbers, colorants, fragrances and preservatives.

33. The composition according to claim 26 wherein said composition is a deodorant, antiperspirant, sunscreen, insect repellent or anti-fungal agent.

34. The composition according to claim 26 wherein said isoparaffin has a flash point in the range between about 60 to 150° C. and said non-volatile silicone fluid has a viscosity of no greater than 10,000 cSt.

* * * * *